United States Patent
Shibahara et al.

(10) Patent No.: US 9,393,078 B2
(45) Date of Patent: Jul. 19, 2016

(54) LIGHT SOURCE APPARATUS FOR MEDICAL USE

(71) Applicant: HOYA CORPORATION, Tokyo (JP)

(72) Inventors: Yoshitaka Shibahara, Tokyo (JP); Hiroyuki Watanabe, Tokyo (JP); Hidenori Takushima, Saitama (JP)

(73) Assignee: HOYA CORPORATION, Tokyo (JP)

( * ) Notice: Subject to any disclaimer, the term of this patent is extended or adjusted under 35 U.S.C. 154(b) by 115 days.

(21) Appl. No.: 14/183,926

(22) Filed: Feb. 19, 2014

(65) Prior Publication Data

US 2014/0249376 A1 Sep. 4, 2014

(30) Foreign Application Priority Data

Mar. 4, 2013 (JP) ................................ 2013-041657

(51) Int. Cl.
| | | |
|---|---|---|
| A61B 19/00 | (2006.01) | |
| A61B 1/00 | (2006.01) | |
| A61B 1/06 | (2006.01) | |
| A61B 17/00 | (2006.01) | |

(52) U.S. Cl.
CPC ......... *A61B 19/5202* (2013.01); *A61B 1/00059* (2013.01); *A61B 1/00124* (2013.01); *A61B 1/00126* (2013.01); *A61B 1/0646* (2013.01); *A61B 1/0669* (2013.01); *A61B 1/0661* (2013.01); *A61B 2017/00482* (2013.01)

(58) Field of Classification Search
CPC ............. A61B 1/0669; A61B 1/00059; A61B 1/00126; A61B 1/00124; A61B 1/0646; A61B 19/5202; A61B 2019/5206; A61B 2019/521; A61B 2017/00482; A61B 2017/00477; A61B 1/0661

USPC ................... 600/249, 180, 118, 178; 606/166
See application file for complete search history.

(56) References Cited

U.S. PATENT DOCUMENTS

| | | | | |
|---|---|---|---|---|
| 4,791,479 | A * | 12/1988 | Ogiu ........................ | A61B 1/05 348/270 |
| 4,816,909 | A * | 3/1989 | Kimura et al. ................... | 348/71 |
| 4,866,526 | A * | 9/1989 | Ams ........................ | A61B 1/05 348/364 |
| 8,525,875 | B2 * | 9/2013 | Kawata et al. ................... | 348/65 |
| 8,537,210 | B2 | 9/2013 | Omori et al. | |
| 2004/0064019 | A1 * | 4/2004 | Chang et al. .................. | 600/180 |
| 2012/0245609 | A1 * | 9/2012 | Brown .......................... | 606/166 |

FOREIGN PATENT DOCUMENTS

| | | |
|---|---|---|
| JP | 09-131320 | 5/1997 |
| JP | 2006-075239 | 3/2006 |

* cited by examiner

*Primary Examiner* — Todd E Manahan
*Assistant Examiner* — Marcela I Shirsat
(74) *Attorney, Agent, or Firm* — Greenblum & Bernstein, P.L.C.

(57) ABSTRACT

A medical-use light-source apparatus includes a light source lamp, a connector to which a body cavity endoscope and an ophthalmic observation apparatus can be selectively connected, a determiner which determines whether the body cavity endoscope or the ophthalmic observation apparatus is currently connected to the connector, and a lamp controller which sets a value of a maximum light amount of the illumination light to a first threshold value when the determiner determines that the body cavity endoscope is currently connected to the connector, and sets a value of a maximum light amount of the illumination light to a second threshold value that is smaller than the first threshold value when the determiner determines that the ophthalmic observation apparatus is currently connected to the connector.

9 Claims, 3 Drawing Sheets

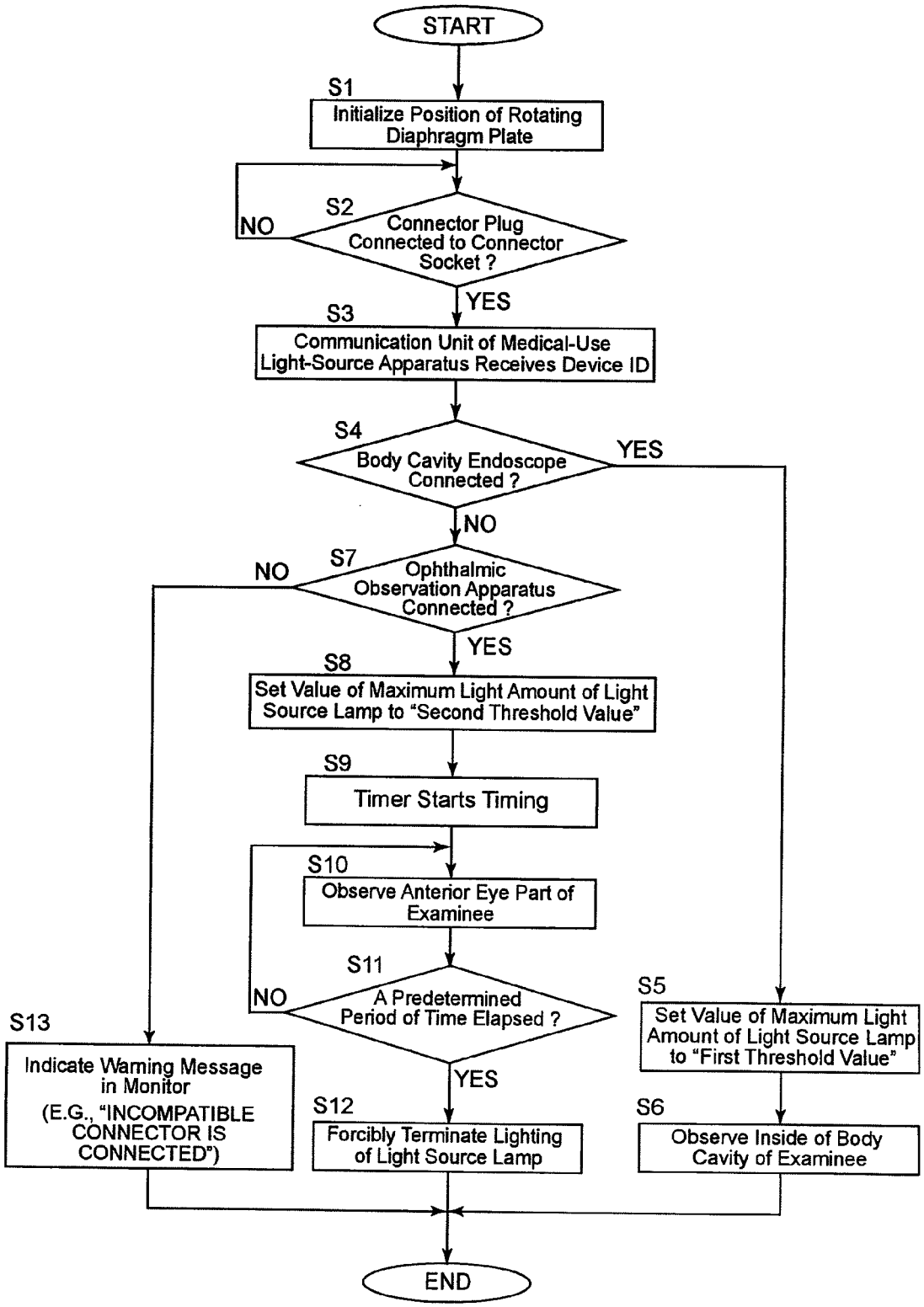

LIGHT SOURCE APPARATUS FOR MEDICAL USE

BACKGROUND OF THE INVENTION

1. Field of the Invention

The present invention relates to a light source apparatus for medical use which can be used in common in a body cavity endoscope and in an ophthalmic observation apparatus.

2. Description of the Related Art

Body cavity endoscopes (endoscopes designed for observing inside a body cavity) are for diagnosing the presence or absence of lesions and observing the state thereof while emitting illumination light in a body cavity (e.g., digestive canal) in the examinee (patient). Ophthalmic observation apparatuses are for diagnosing eye diseases such as glaucoma, retinal detachment and fundal hemorrhage of the eye by observing the state of blood vessels, retina and optic nerves in the ocular fundus while applying illumination light to an anterior eye part of the examinee. Conventionally, a light source apparatus used to supply illumination light to a body cavity endoscope and a light source apparatus used to supply illumination light to an ophthalmic observation apparatus have been separately prepared as special-purpose parts.

The reason why light source apparatuses are separately prepared for a body cavity endoscope and an ophthalmic observation apparatus in such a manner in convention systems is that the light quantity (luminous intensity) of illumination light required for body cavity endoscopes and the light quantity (luminous intensity) of light for the illumination required for ophthalmic observation apparatuses are considerably different from each other. Specifically, if an ophthalmic observation apparatus that operates well with a small quantity of light is mistakenly connected to a light source apparatus designed for body cavity endoscope that supplies illumination light which is great in light quantity (luminous intensity), one cannot visually observe the eyes of an examinee because reflected light of the illumination light by the crystalline lens is excessively great; moreover, there is a possibility of the eyes of the examinee being damaged. Therefore, it has been technical common sense to not to provide compatibility between the light source connectors of both light source apparatuses so that no ophthalmic observation apparatuses can be connected to a light source apparatus designed for body cavity endoscopes. However, if a light source apparatus (light source lamp) can be made available for both a body cavity endoscope and an ophthalmic observation apparatus, convenience in both power management and equipment investment would increase.

SUMMARY OF THE INVENTION

The present invention has been devised in consideration of the above viewpoint and provides a medical-use light-source apparatus which can be connected to each of a body cavity endoscope and an ophthalmic observation apparatus, and which sets an optimum light quantity (luminous intensity) of illumination light by detecting whether a body cavity endoscope or an ophthalmic observation apparatus is currently connected, which makes it possible to achieve satisfactory visual observation of the eyes of an examinee without fear of damaging the eyes of the examinee when an ophthalmic observation apparatus, in particular, is used.

According to an aspect of the present invention, a medical-use light-source apparatus is provided, including a light source lamp which emits illumination light; a connector to which a body cavity endoscope that emits the light in a body cavity of an examinee and an ophthalmic observation apparatus that emits the light toward an anterior eye part of an examinee can be selectively connected; a determiner which determines whether the body cavity endoscope or the ophthalmic observation apparatus is currently connected to the connector; and a lamp controller which sets a value of a maximum light amount of the illumination light that the light source lamp supplies to the body cavity endoscope to a first threshold value when the determiner determines that the body cavity endoscope is currently connected to the connector, and sets a value of a maximum light amount of the illumination light that the light source lamp supplies to the ophthalmic observation apparatus to a second threshold value that is smaller than the first threshold value when the determiner determines that the ophthalmic observation apparatus is currently connected to the connector.

In the present application, the expression "a body cavity endoscope or an ophthalmic observation apparatus is currently connected to a connector" means that a body cavity endoscope or an ophthalmic observation apparatus is currently connected to a connector (of a medical-use light-source apparatus) in a state of being supplied with illumination light from a light source lamp and is capable of emitting this light.

In the case where the light source lamp supplies illumination light to the ophthalmic observation apparatus, it is desirable for the lamp controller to forcibly turn OFF the light source lamp when the light source lamp remains ON for a predetermined period of time.

It is desirable for the medical-use light-source apparatus to include a communication unit which communicates with the body cavity endoscope and the ophthalmic observation apparatus when the body cavity endoscope and the ophthalmic observation apparatus are connected to the connector, respectively. The determiner determines whether the body cavity endoscope or the ophthalmic observation apparatus is currently connected to the connector based on a result of the communication carried out by the communication unit.

According to the present invention, a medical-use light-source apparatus is achieved, which can be connected to each of a body cavity endoscope and an ophthalmic observation apparatus, and which sets an optimum light quantity (luminous intensity) of illumination light by detecting whether a body cavity endoscope or an ophthalmic observation apparatus is currently connected, which makes it possible to achieve favorable visual observation of the eyes of an examinee without fear to damage the eyes especially when an ophthalmic observation apparatus is used.

The present disclosure relates to subject matter contained in Japanese Patent Application No. 2013-41657 (filed on Mar. 4, 2013) which is expressly incorporated herein by reference in its entirety.

BRIEF DESCRIPTION OF THE DRAWINGS

The present invention will be described below in detail with reference to the accompanying drawings in which:

FIG. 3 is a flow chart showing operations of the medical-use light-source apparatus according to the present invention.

DESCRIPTION OF THE PREFERRED EMBODIMENT

Figure 1:
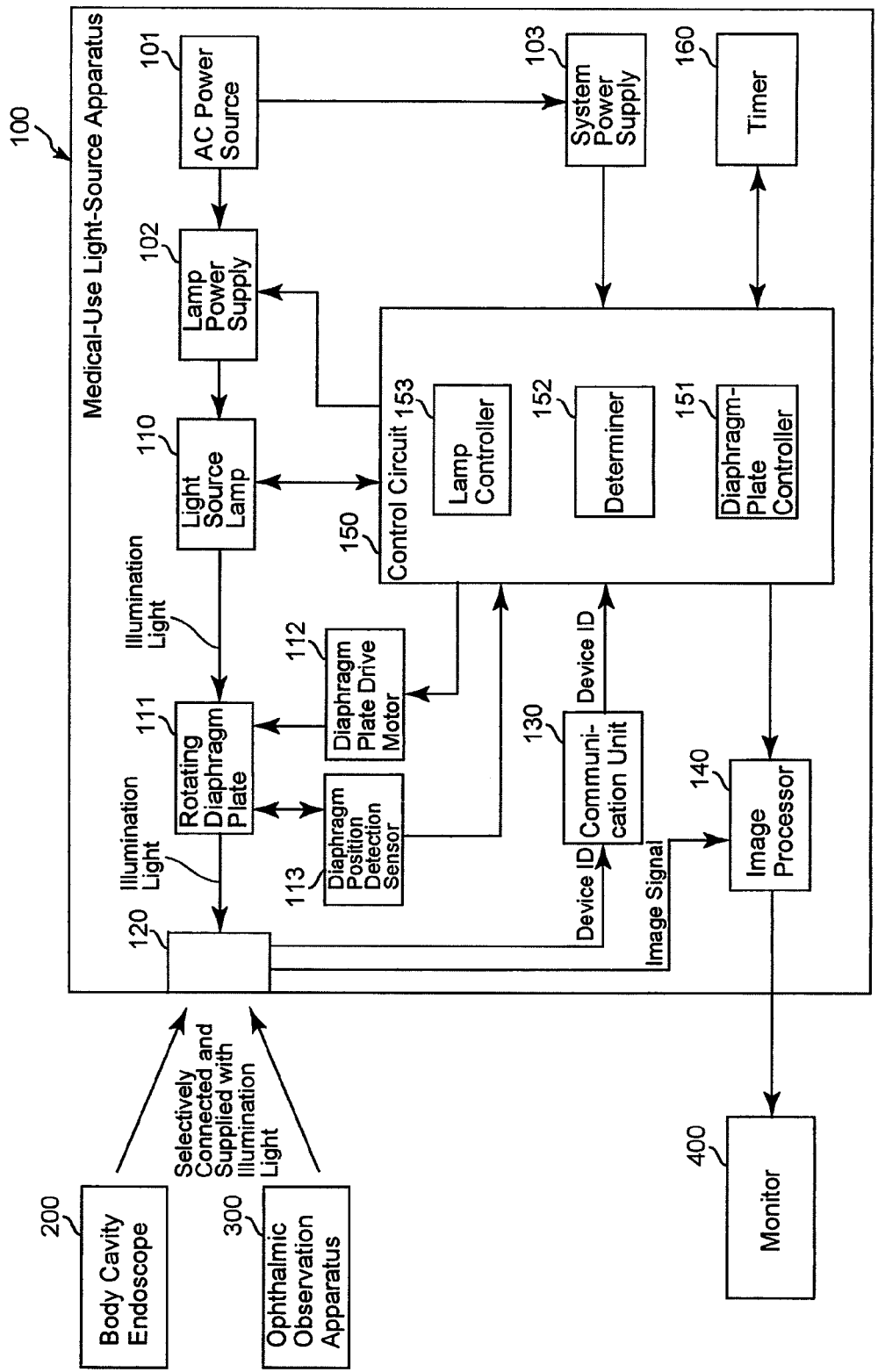
FIG. 1 is a block diagram schematically showing the structure of a medical-use light-source apparatus according to the present invention.

The structure of a medical-use light-source apparatus (processor) 100 according to the present invention will be hereinafter discussed with reference to FIGS. 1, 2A and 2B.

The medical-use light-source apparatus 100 is provided with an AC power source 101 which serves as a power source for driving all the components of the medical-use light-source apparatus 100, a lamp power supply 102 which supplies power received from the AC power source 101 to a lamp system of the medical-use light-source apparatus 100, and a system power supply 103 which supplies power received from the AC power source 101 to a control circuit (main controller) 150 (of a control system) of the medical-use light-source apparatus 100.

The medical-use light-source apparatus 100 is provided with a light source lamp 110 which emits illumination light using power supplied from the lamp power supply 102. The light source lamp 110 can be, e.g., a halogen lamp, a xenon lamp or an LED lamp. The light source lamp 110 is configured to be capable of varying the light quantity (luminous intensity) of illumination light emitted therefrom.

The medical-use light-source apparatus 100 is provided with a rotating diaphragm plate (rotating chopper) 111 for adjusting the light quantity of the illumination light that is emitted by the light source lamp 110, a diaphragm plate drive motor 112 which drives and rotates the rotating diaphragm plate 111, and a diaphragm position detection sensor 113 which detects the rotational position of the rotating diaphragm plate 111.

The medical-use light-source apparatus 100 is provided with a connector socket (connector) 120 which includes a light guide path. A body cavity endoscope 200 and an ophthalmic observation apparatus 300 can be selectively connected to the connector socket 120. More specifically, as shown in FIGS. 2A and 2B, the body cavity endoscope 200 and the ophthalmic observation apparatus 300 are provided with a connector plug (connector) 210 and a connector plug (connector) 310, respectively, which are identical in specifications to be freely selectively connected to the connector socket 120 (i.e., to provide compatibility to the connector plugs 210 and 310). In addition, an ID memory 211, in which a device ID unique to the body cavity endoscope 200 is stored, is embedded in the connector plug 210, and an ID memory 311, in which a device ID unique to the ophthalmic observation apparatus 300 is stored, is embedded in the connector plug 310. The medical-use light-source apparatus 100 is provided with a communication unit 130 which can communicate with the ID memory 211 when the body cavity endoscope 200 is connected to the medical-use light-source apparatus 100 and can communicate with the ID memory 311 when the ophthalmic observation apparatus 300 is connected to the medical-use light-source apparatus 100. Due to the communication unit 130 receiving either device ID by communicating with the ID memory 211 or 311, the medical-use light-source apparatus 100 can determine whether the apparatus currently connected to the medical-use light-source apparatus 100 (the connector socket 120) is the body cavity endoscope 200 (the connector plug 210) or the ophthalmic observation apparatus 300 (the connector plug 310).

Information on the length of the insertion portion of the body cavity endoscope 200 or the ophthalmic observation apparatus 300 and information on the doctor(s) who uses the body cavity endoscope 200 or the ophthalmic observation apparatus 300 can be device ID information stored in the ID memories 211 and 311.

Figure 2A:
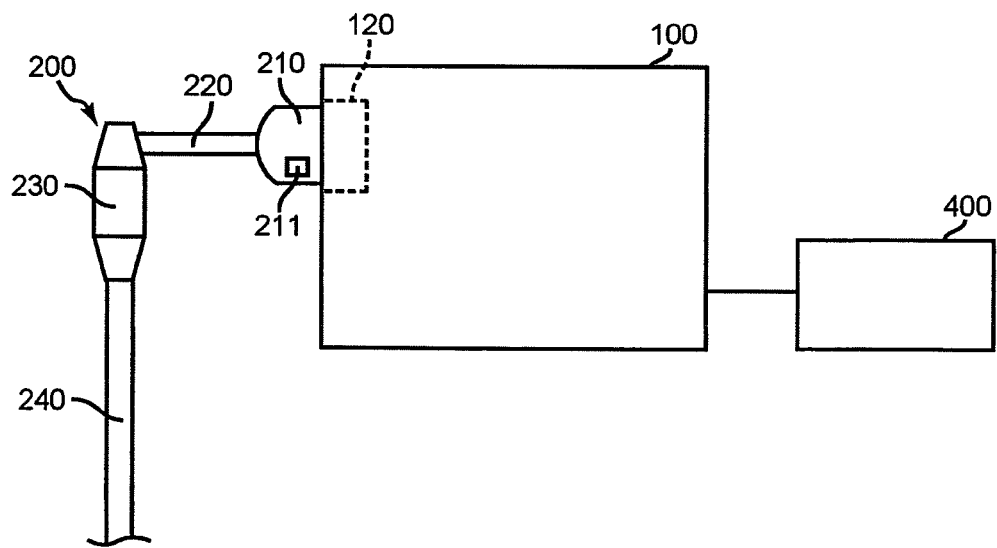
FIG. 2A is a schematic diagram showing a state where a body cavity endoscope is connected to a connector of the medical-use light-source apparatus.

When the body cavity endoscope 200 is connected to the medical-use light-source apparatus 100 (as shown in FIG. 2A), illumination light which is emitted from the light source lamp 110 is incident, via the rotating diaphragm plate 111 and the light guide path of the connector socket 120, on a fiber optic light guide (not shown) which extends from a universal cable 220 to the distal end of the insertion portion 240 via a controller 230 of the body cavity endoscope 200 to consequently emerge from an illumination lens (not shown) which is provided at the distal end of the fiber optic light guide. The illumination light emerging from the illumination lens illuminates the inside of a body cavity (e.g., digestive canal) of the examinee, and light reflected thereby is imaged by an image sensor (not shown) provided at the distal end of the insertion portion 240 and is converted into an image signal. This image signal is transmitted by an image signal transmission cable (not shown) which extends from the insertion portion 240 of the body cavity endoscope 200 to an image processor 140 (which is provided in the medical-use light-source apparatus 100) via the controller 230 and the universal cable 220 of the body cavity endoscope 200.

Figure 2B:
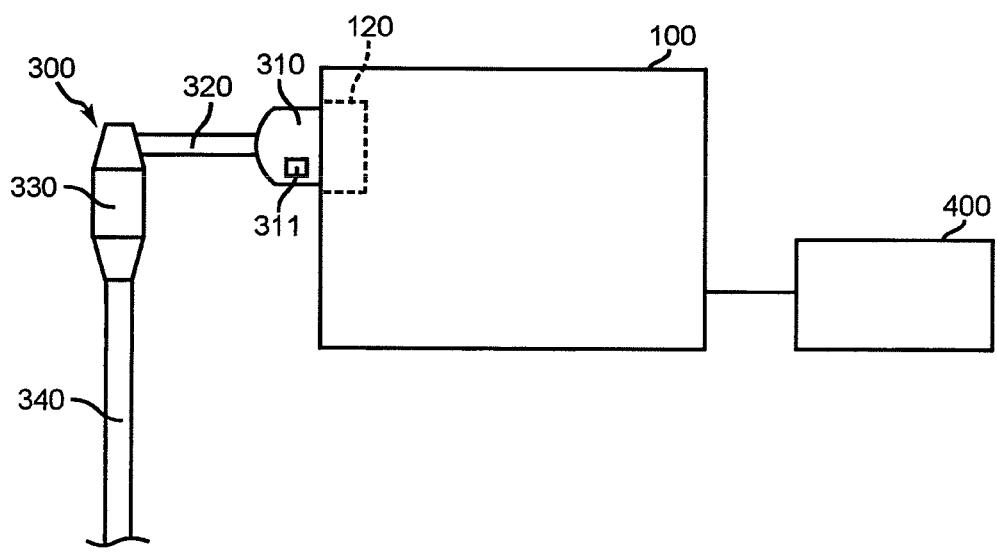
FIG. 2B is a schematic diagram showing a state where an ophthalmic observation apparatus is connected to the same connector of the medical-use light-source apparatus.

When the ophthalmic observation apparatus 300 is connected to the medical-use light-source apparatus 100 (as shown in FIG. 2B), illumination light which is emitted from the light source lamp 110 is incident, via the rotating diaphragm plate 111 and the light guide path of the connector socket 120, on a fiber optic light guide (not shown) which extends from a universal cable 320 to the distal end of the insertion portion 340 via a controller 330 of the ophthalmic observation apparatus 300 to consequently emerge from an illumination lens (not shown) which is provided at the distal end of the fiber optic light guide. The illumination light emerging from the illumination lens illuminates an anterior eye part of the examinee, and light reflected thereby is imaged by an image sensor (not shown) provided at the distal end of the insertion portion 340 and is converted into an image signal. This image signal is transmitted by an image signal transmission cable (not shown) which extends from the insertion portion 340 of the body cavity endoscope 300 to the image processor 140 (which is provided in the medical-use light-source apparatus 100) via the controller 330 and the universal cable 320 of the ophthalmic observation apparatus 300.

The image processor 140 performs image processing on the image signal transmitted thereto from the image signal transmission cable of the body cavity endoscope 200 or the ophthalmic observation apparatus 300, and the observed image on which image processing has been performed by the image processor 140 is displayed on a monitor 400 provided outside the medical-use light-source apparatus 100.

The control circuit 150 (provided in the medical-use light-source apparatus 100) controls the overall operation of the medical-use light-source apparatus 100. The control circuit 150 is provided with a diaphragm-plate controller 151, a determiner 152 and a lamp controller 153.

The diaphragm-plate controller 151 controls the rotational driving of the rotating diaphragm plate 111 via the diaphragm plate drive motor 112 according to the rotational position of the rotating diaphragm plate 111 that is detected by the diaphragm position detection sensor 113.

The determiner 152 determines whether the body cavity endoscope 200 (the connector plug 210) or the ophthalmic observation apparatus 300 (the connector plug 310) is currently connected to the medical-use light-source apparatus 100 (the connector socket 120).

Based on the determination by the determiner 152, the lamp controller 153 sets the maximum light amount (maximum luminous intensity) of illumination light that the light source lamp 110 supplies to the body cavity endoscope 200 or the ophthalmic observation apparatus 300.

Specifically, the lamp controller 153 sets the value of the maximum light amount (maximum luminous intensity) of illumination light that the light source lamp 110 supplies to the body cavity endoscope 200 to a "first threshold value" when the determiner 152 determines that the body cavity endoscope 200 (the connector plug 210) is currently connected to the medical-use light-source apparatus 100 (the connector socket 120). The "first threshold value" can be, e.g., the maximum light quantity (luminous intensity) of illumination light that the light source lamp 110 can supply.

On the other hand, the lamp controller 153 sets the value of the maximum light amount (maximum luminous intensity) of illumination light that the light source lamp 110 supplies to the ophthalmic observation apparatus 300 to a "second threshold value" that is smaller than the first threshold value when the determiner 152 determines that the ophthalmic observation apparatus 300 (the connector plug 310) is currently connected to the medical-use light-source apparatus 100 (the connector socket 120).

In the present embodiment, the "first threshold value" and the "second threshold value" are set to 800 cd (candela) and 1 cd (candela), respectively.

When the light source lamp 110 supplies illumination light to the ophthalmic observation apparatus 300, the lamp controller 153 forcibly turns OFF the light source lamp 110 in the case where the light source lamp 110 remains ON for a predetermined period of time. Specifically, the lamp controller 153 starts a timer 160 to time the instant the light source lamp 110 commences to supply illumination light to the ophthalmic observation apparatus 300, and subsequently the lamp controller 153 forcibly turns OFF the light source lamp 110 immediately after the continuous lighting time of the light source lamp 110 reaches a predetermined period of time (e.g., five minutes).

When the determiner 152 determines that the body cavity endoscope 200 (the connector plug 210) is currently connected to the medical-use light-source apparatus 100 (the connector socket 120), the lamp controller 153 controls lighting of the light source lamp 110 to allow the light source lamp 110 to be selectively switched between a continuous lighting mode and a blinking mode. One can switch the light source lamp 110 between the continuous lighting mode and the blinking mode by manually operating a manual switch (not shown).

On the other hand, when the determiner 152 determines that the ophthalmic observation apparatus 300 (the connector plug 310) is currently connected to the medical-use light-source apparatus 100 (the connector socket 120), the lamp controller 153 controls lighting of the light source lamp 110 so that the light source lamp 110 always illuminates in the continuous lighting mode. In a state where the ophthalmic observation apparatus 300 is connected to the medical-use light-source apparatus 100, if an operation switching from the continuous lighting mode to the blinking mode is manually performed with a manual switch (not shown), the lamp controller 153 visually indicates a warning message such as "WARNING! ARE YOU SURE YOU WANT TO SWITCH TO BLINKING MODE THOUGH CURRENTLY USING OPHTHALMIC OBSERVATION APPARATUS?", on the monitor 400 to request reconfirmation from the user, and allows the light source lamp 110 to blink exceptionally, only when reconfirmation is obtained from the user.

Operations of the medical-use light-source apparatus 100 that has the above described structure will be hereinafter discussed with reference to the flow chart shown in FIG. 3.

Upon the power of the medical-use light-source apparatus 100 being turned ON, the diaphragm-plate controller 151 initializes the rotational position of the rotating diaphragm plate 111 via the diaphragm plate drive motor 112 (step S1).

Subsequently, the communication unit 130 determines whether or not a connector plug having communication capability is currently connected to the connector socket 120 (step S2). If such a connector plug is not currently connected to the connector socket 120 (if NO at step S2), the communication unit 130 does not perform any operation (control repeats the operation at step S2). When such a connector plug is connected to the connector socket 120 (if YES at step S2), the communication unit 130 receives a device ID from the currently-connected connector plug (step S3).

Subsequently, the determiner 152 determines whether or not the body cavity endoscope 200 (the connector plug 210) is currently connected to the medical-use light-source apparatus 100 (the connector socket 120) based on the result of the communication of the communication unit 130 (step S4). If the determiner 152 determines that the body cavity endoscope 200 (the connector plug 210) is currently connected to the medical-use light-source apparatus 100 (the connector socket 120) (if YES at step S4), the lamp controller 153 sets the value of the maximum light amount (maximum luminous intensity) of illumination light that the light source lamp 110 supplies to the body cavity endoscope 200 to the "first threshold value" (step S5), and thereafter, the inside of a body cavity (e.g., digestive canal) of the examinee is observed (step S6).

If the determiner 152 determines that the body cavity endoscope 200 (the connector plug 210) is not currently connected to the medical-use light-source apparatus 100 (the connector socket 120) (if NO at step S4), the determiner 152 determines whether or not the ophthalmic observation apparatus 300 (the connector plug 310) is currently connected to the medical-use light-source apparatus 100 (the connector socket 120) (step S7). If the determiner 152 determines that the ophthalmic observation apparatus 300 (the connector plug 310) is currently connected to the medical-use light-source apparatus 100 (the connector socket 120) (if YES at step S7), the lamp controller 153 sets the value of the maximum light amount (maximum luminous intensity) of illumination light that the light source lamp 110 supplies to the ophthalmic observation apparatus 300 to the "second threshold value" that is smaller than the first threshold value (step S8), and the lamp controller 153 makes the timer 160 start timing (step S9), and thereafter, an anterior eye part of the examinee is observed (step S10).

Referring to the timer 160, the lamp controller 153 controls lighting of the light source lamp 110 so that the light source lamp 110 continues to illuminate to enable an anterior eye part of the examinee to be observed until the continuous lighting time of the light source lamp 110 reaches a predetermined period of time (e.g., five minutes) (if NO at step S11; and step S10). Upon a lapse of the continuous lighting time of the light source lamp 110 (e.g., five minutes), the lamp controller 153 forcibly turns OFF the light source lamp 110 so that the anterior eye part of the examinee cannot be observed (YES at step S11; and step S12).

If the determiner 152 determines that the ophthalmic observation apparatus 300 (the connector plug 310) is not currently connected to the medical-use light-source apparatus 100 (the connector socket 120) (if NO at step S7), this means that an endoscope or another type of apparatus which cannot be used (i.e., is incompatible) with the medical-use light-source apparatus 100 is currently connected to the medical-use light-source apparatus 100, and accordingly, a warning message such as "INCOMPATIBLE CONNECTOR IS CONNECTED" is visually indicated on the monitor 400 (step S13).

As described above, according to the present embodiment of the medical-use light-source apparatus 100, the lamp controller 153 sets the value of the maximum light amount (maximum luminous intensity) of illumination light that the light source lamp 110 supplies to the body cavity endoscope 200 to the "first threshold value" when the determiner 152 determines that the body cavity endoscope 200 is currently connected to the connector socket (connector) 120, and the lamp controller 153 sets the value of the maximum light amount (maximum luminous intensity) of illumination light that the light source lamp 110 supplies to the ophthalmic observation apparatus 300 to the "second threshold value", which is smaller than the first threshold value, when the determiner 152 determines that the ophthalmic observation apparatus 300 is currently connected to the connector socket (connector) 120. This makes it possible to set an optimum light quantity (luminous intensity) of illumination light for each of the body cavity endoscope 200 and the ophthalmic observation apparatus 300 and thereby to achieve satisfactory visual observation of the eyes of an examinee without fear of damaging the eyes especially when the ophthalmic observation apparatus 300 is used.

Additionally, when the light source lamp 110 supplies illumination light to the ophthalmic observation apparatus 300, the lamp controller 153 forcibly turns OFF the light source lamp 110 in the case where the light source lamp 110 remains ON for a predetermined period of time, which makes it possible to achieve satisfactory visual observation of the eyes of the examinee without fear of damaging the eyes due to careless continuous lighting of the light source lamp 110.

The above embodiment of the medical-use light-source apparatus 100 has been discussed by illustrating the case where the "first threshold value" and the "second threshold value" are set to 800 cd (candela) and 1 cd (candela), respectively. However, these threshold values are merely examples; various modifications to the aforementioned specific values of the "first threshold value" and the "second threshold value" are possible.

The above embodiment of the medical-use light-source apparatus 100 has been discussed by illustrating the case where the lamp controller 153 forcibly turns OFF the light source lamp 110 upon a lapse of the continuous lighting time of the light source lamp 110 (e.g., five minutes); however, the continuous lighting time of the light source lamp 110 is not limited to five minutes, and various design changes to the lighting control are possible. The continuous lighting time of the light source lamp 110 is determined in consideration of safety aspects based on the dose of exposure to the retina which is defined by the product of the intensity of radiation and the exposure time of the light source lamp 110.

Although the above embodiment of the medical-use light-source apparatus 100 has been discussed by illustrating the case where the medical-use light-source apparatus 100 is provided with the single connector socket 120 that can be shared between the body cavity endoscope 200 and the ophthalmic observation apparatus 300, it is possible to provide the medical-use light-source apparatus 100 with two separate special-purpose connectors designed exclusively for the body cavity endoscope 200 and the ophthalmic observation apparatus 300, respectively. In this case, upon the connector plug 210 or 310 of the body cavity endoscope 200 or the ophthalmic observation apparatus 300 being plugged into the associated special-purpose connector, the determiner 152 determines this event, and thereupon the lamp controller 153 sets the value of the maximum light amount (maximum luminous intensity) of illumination light that the light source lamp 110 supplies to the body cavity endoscope 200 or the ophthalmic observation apparatus 300 to the "first threshold value" or the "second threshold value", respectively. In this case, since there is only one light source lamp 110 provided on the medical-use light-source apparatus 100, even when both the body cavity endoscope 200 and the ophthalmic observation apparatus 300 are connected to the respective special-purpose connectors of the medical-use light-source apparatus 100, only one of the body cavity endoscope 200 and the ophthalmic observation apparatus 300 can receive illumination light from the light source lamp 100 and emit this illumination light at a time.

Obvious changes may be made in the specific embodiment of the present invention described herein, such modifications being within the spirit and scope of the invention claimed. It is indicated that all matter contained herein is illustrative and does not limit the scope of the present invention.

What is claimed is:

1. A medical-use light-source apparatus comprising:
   a variable output light source including a light source lamp which emits a variable amount of illumination light;
   a connector to which a body cavity endoscope that emits the illumination light in a body cavity of an examinee and an ophthalmic observation apparatus that emits the illumination light toward an anterior eye part of an examinee can be selectively connected;
   a determiner which determines whether said body cavity endoscope or said ophthalmic observation apparatus is currently connected to said connector; and
   a lamp controller which sets a value of a maximum light amount of the illumination light that said light source lamp emits and supplies to said body cavity endoscope to a first threshold value when said determiner determines that said body cavity endoscope is currently connected to said connector, and sets a value of a maximum light amount of the illumination light that said light source lamp emits and supplies to said ophthalmic observation apparatus to a second threshold value that is smaller than said first threshold value when said determiner determines that said ophthalmic observation apparatus is currently connected to said connector,
   wherein,
   when the light source lamp supplies illumination light to the body cavity endoscope, the lamp controller controls the light source lamp to switch between a continuous lighting operation and a blinking operation, and
   when the light source lamp supplies illumination light to the ophthalmic observation apparatus, the lamp controller controls the light source lamp to remain in the continuous lighting operation.

2. The medical-use light-source apparatus according to claim 1, wherein when said light source lamp supplies illumination light to said ophthalmic observation apparatus, said lamp controller forcibly turns OFF said light source lamp when said light source lamp remains ON for a predetermined period of time.

3. The medical-use light-source apparatus according to claim 1, further comprising a communicator which communicates with said body cavity endoscope and said ophthalmic observation apparatus when said body cavity endoscope and said ophthalmic observation apparatus are connected to said connector, respectively, and wherein said determiner determines whether said body cavity endoscope or said ophthalmic observation apparatus is currently connected to said connector based on a result of the communication by said communicator.

4. The medical-use light-source apparatus according to claim 1, wherein the light source lamp emits illumination light of a variable amount, the variable amount including a range between 1 cd to 800 cd.

5. The medical-use light-source apparatus according to claim 1, wherein the first threshold value is a three digit value, and the second threshold value is a single digit value.

6. The medical-use light-source apparatus according to claim 1, wherein the first threshold value is a maximum light amount that the light source lamp is capable of emitting.

7. The medical-use light-source apparatus according to claim 1, further comprising:
 a diaphragm plate that adjusts the light amount of the illumination light emitted by the light source lamp; and
 a diaphragm plate controller that controls a rotational position of the diaphragm plate.

8. The medical-use light-source apparatus according to claim 1, further comprising a switch that switches the light source lamp between the continuous lighting and blinking operations,
 wherein when the light source lamp supplies illumination light to the ophthalmic observation apparatus, and the switch is operated to switch from the continuous lighting operation to the blinking operation, a warning message is provided.

9. The medical-use light-source apparatus according to claim 1, wherein when the determiner determines that a device, which is other than the body cavity endoscope and the ophthalmic observation apparatus is currently connected to the connector, a warning message is provided indicating that an incompatible device is connected.

* * * * *